(12) United States Patent
Locke et al.

(10) Patent No.: US 12,178,598 B2
(45) Date of Patent: Dec. 31, 2024

(54) NEGATIVE-PRESSURE SYSTEM INCORPORATING WOUND DIAGNOSTIC CAPABILITIES

(71) Applicant: Solventum Intellectual Properties Company, Maplewood, MN (US)

(72) Inventors: Christopher Brian Locke, Bournemouth (GB); Richard Daniel John Coulthard, Verwood (GB); Timothy Mark Robinson, Shillingstone (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 21 days.

(21) Appl. No.: 17/631,923

(22) PCT Filed: Aug. 3, 2020

(86) PCT No.: PCT/IB2020/057325
§ 371 (c)(1),
(2) Date: Feb. 1, 2022

(87) PCT Pub. No.: WO2021/028773
PCT Pub. Date: Feb. 18, 2021

(65) Prior Publication Data
US 2022/0280712 A1  Sep. 8, 2022

Related U.S. Application Data

(60) Provisional application No. 62/885,015, filed on Aug. 9, 2019.

(51) Int. Cl.
*A61M 1/00* (2006.01)
*A61B 5/00* (2006.01)

(52) U.S. Cl.
CPC ............... *A61B 5/445* (2013.01); *A61M 1/60* (2021.05); *A61M 1/73* (2021.05); *A61M 1/918* (2021.05);
(Continued)

(58) Field of Classification Search
CPC ... A61B 5/445; A61B 5/0059; A61B 2562/02; A61B 5/14539; A61M 1/60; A61M 1/73;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

R. Bagherzadeh, M. Gorji, M.S. Sorayani Bafgi, N. Saveh-Shemshaki, Electrospun conductive nanofibers for electronics, 2017, Woodhead Publishing, pp. 467-519 (Year: 2017).*

(Continued)

*Primary Examiner* — Nicholas J. Weiss
*Assistant Examiner* — Brandon W. Levy

(57) ABSTRACT

A therapy system for treating a tissue site with negative-pressure therapy and/or fluid instillation therapy in response to information received from a diagnostic module is described. The therapy system may include a dressing, a negative-pressure source, a container, and a diagnostic module. The dressing be placed on the tissue site, and the negative-pressure source may be fluidly coupled to the dressing. The container may be fluidly coupled to the dressing and to the negative-pressure source to receive fluid (Continued)

from the tissue site. The diagnostic module may be exposed to gas associated with the fluid from the tissue site. The diagnostic module may comprise a sensor configured to detect a condition of the tissue site and to generate an output based on the detected condition. The sensor may be configured to detect a volatile organic compound. The diagnostic module may be positioned on the container.

17 Claims, 6 Drawing Sheets

(52) U.S. Cl.
CPC ............... *A61M 1/92* (2021.05); *A61M 1/95* (2021.05); *A61M 1/962* (2021.05); *A61M 1/966* (2021.05); *A61M 1/982* (2021.05); *A61M 1/784* (2021.05); *A61M 2205/3306* (2013.01); *A61M 2205/3375* (2013.01)

(58) Field of Classification Search
CPC .......... A61M 1/918; A61M 1/92; A61M 1/95; A61M 1/962; A61M 1/966; A61M 1/982; A61M 1/784; A61M 2205/3306; A61M 2205/3375; A61M 2205/3303; A61M 2205/3324; A61M 1/96; A61M 1/71–1/98; A61M 1/74; A61M 1/915; A61M 2205/3331; A61M 2205/18; A61M 2205/3334; A61M 1/90; A61M 2205/7536; A61M 1/78; A61F 13/00068; A61F 2013/00174; A61F 13/0216; A61F 2013/00536; A61F 13/02; A61F 2013/0054; A61F 13/05; A61P 17/02; Y10T 137/3003; Y10T 137/3084; Y10T 137/309

See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,611,846 A * | 3/1997 | Overton ................. | G01N 30/68 95/82 |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,052,932 B2 | 11/2011 | Han et al. | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |

(56) References Cited

U.S. PATENT DOCUMENTS

| | | | |
|---|---|---|---|
| 8,632,512 B2* | 1/2014 | Zimnitsky | A61P 29/00 |
| | | | 602/56 |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1* | 10/2002 | Tumey | A61B 5/445 |
| | | | 128/850 |
| 2006/0015019 A1* | 1/2006 | Watt | A61M 1/73 |
| | | | 600/309 |
| 2010/0049150 A1* | 2/2010 | Braga | A61M 1/784 |
| | | | 604/313 |
| 2010/0150991 A1* | 6/2010 | Bernstein | A61M 1/95 |
| | | | 604/23 |
| 2010/0174270 A1* | 7/2010 | Charlez | A61M 1/61 |
| | | | 604/540 |
| 2011/0015591 A1* | 1/2011 | Hanson | A61B 5/150251 |
| | | | 604/319 |
| 2013/0066349 A1* | 3/2013 | Fink | A61B 5/445 |
| | | | 606/169 |
| 2013/0267918 A1* | 10/2013 | Pan | A61M 1/74 |
| | | | 604/319 |
| 2014/0163491 A1 | 6/2014 | Schuessler et al. | |
| 2014/0371697 A1 | 12/2014 | Braga et al. | |
| 2015/0080788 A1 | 3/2015 | Blott et al. | |
| 2015/0343144 A1* | 12/2015 | Altschul | A61B 5/4839 |
| | | | 604/503 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | WO-2017197357 A1 * 11/2017 ....... A61F 13/00068 |
| WO | 2019140441 A2 | 7/2019 |

OTHER PUBLICATIONS

International Consensus. The role of proteases in wound diagnostics. An expert working group review. London: Wounds International, 2011.

Gas Sensors Based on Electrospun Nanofibers, Ding et al. Published Mar. 2009, www.mdpi.com/journal/sensors.

International Search Report and Written Opinion Corresponding to Application No. PCT/IB2020/057325, mailed Dec. 23, 2020.

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

(56) References Cited

OTHER PUBLICATIONS

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All—Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

European Office Action for corresponding application 20754032.9, dated Jun. 14, 2024.

\* cited by examiner

NEGATIVE-PRESSURE SYSTEM INCORPORATING WOUND DIAGNOSTIC CAPABILITIES

CROSS-REFERENCE TO RELATED APPLICATIONS

This application claims the benefit of priority to U.S. Provisional Application No. 62/885,015, filed on Aug. 9, 2019, which is incorporated herein by reference in its entirety.

TECHNICAL FIELD

The invention set forth in the appended claims relates generally to tissue treatment systems and more particularly, but without limitation, to sensors and diagnostic apparatuses for wound therapy applications.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a system for treating a tissue site may include a dressing, a negative-pressure source, a container, and a sensor module. The dressing may be adapted to be placed on the tissue site, and the negative-pressure source may be adapted to be fluidly coupled to the dressing. The container may be adapted to be fluidly coupled to the dressing and to the negative-pressure source and to receive fluid from the tissue site. The sensor module may be adapted to be exposed to gas associated with the fluid from the tissue site. The sensor module may comprise a first sensor configured to detect a condition of the tissue site and to generate a first output based on the detected condition. The first sensor may be configured to detect a first volatile organic compound. Additionally, the sensor module may further comprise a second sensor configured to detect a second volatile organic compound. In some embodiments, the sensor module may be positioned on the container.

A canister for collecting fluid from a tissue site is also described herein, herein some example embodiments may include a fluid collection chamber, a first port, a second port, a sensor compartment, and a sensor cartridge. The fluid collection chamber may be adapted to collect and store fluid. The first port may be configured to fluidly connect the fluid collection chamber to a tissue dressing, and the second port may fluidly connect the fluid collection chamber to a negative-pressure source. The sensor compartment may be positioned adjacent to the second port. The sensor cartridge may be configured to be removably inserted in the sensor compartment so as to expose the sensor cartridge to gas associated with the fluid collected in the fluid collection chamber. In some embodiments, the sensor cartridge may comprise a first sensor and a second sensor. The first sensor may detect a first variable related to the tissue site and generate a first output based on the detected first variable, and the second sensor may detect a second variable related to the tissue site and generate a second output based on the detected second variable. Additionally, the canister may further comprise a liquid-air separator positioned between the fluid collection chamber and the sensor compartment. The canister may further include a purge pathway in fluid communication with the sensor compartment for delivering a flow of clean air to the sensor compartment. Additionally, the canister may further comprise a transceiver for wirelessly transmitting a first output related to a condition of the tissue site generated by a first sensor of the senor cartridge.

In further example embodiments, a method of sampling a fluid from a tissue site may include applying a dressing to the tissue site and fluidly connecting the dressing to a negative-pressure source and a canister, which may comprise a fluid collection chamber and a sensor compartment. A sensor module comprising a first sensor may be positioned at least partially within the sensor compartment of the canister, wherein the sensor compartment is exposed to gas contained within the fluid collection chamber. The negative-pressure source may be activated to draw the fluid from the tissue site into the fluid collection chamber, whereby the first sensor is exposed to the gas from the fluid collection chamber. An output from the first sensor related to a detected condition of the gas may be received by a controller. Additionally, the method may further comprise removing the sensor module from the sensor compartment and inserting a replacement sensor module in the sensor compartment. The method may further include recording data related to the detected condition of the gas over a time period.

Objectives, advantages, and a preferred mode of making and using the claimed subject matter may be understood best

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
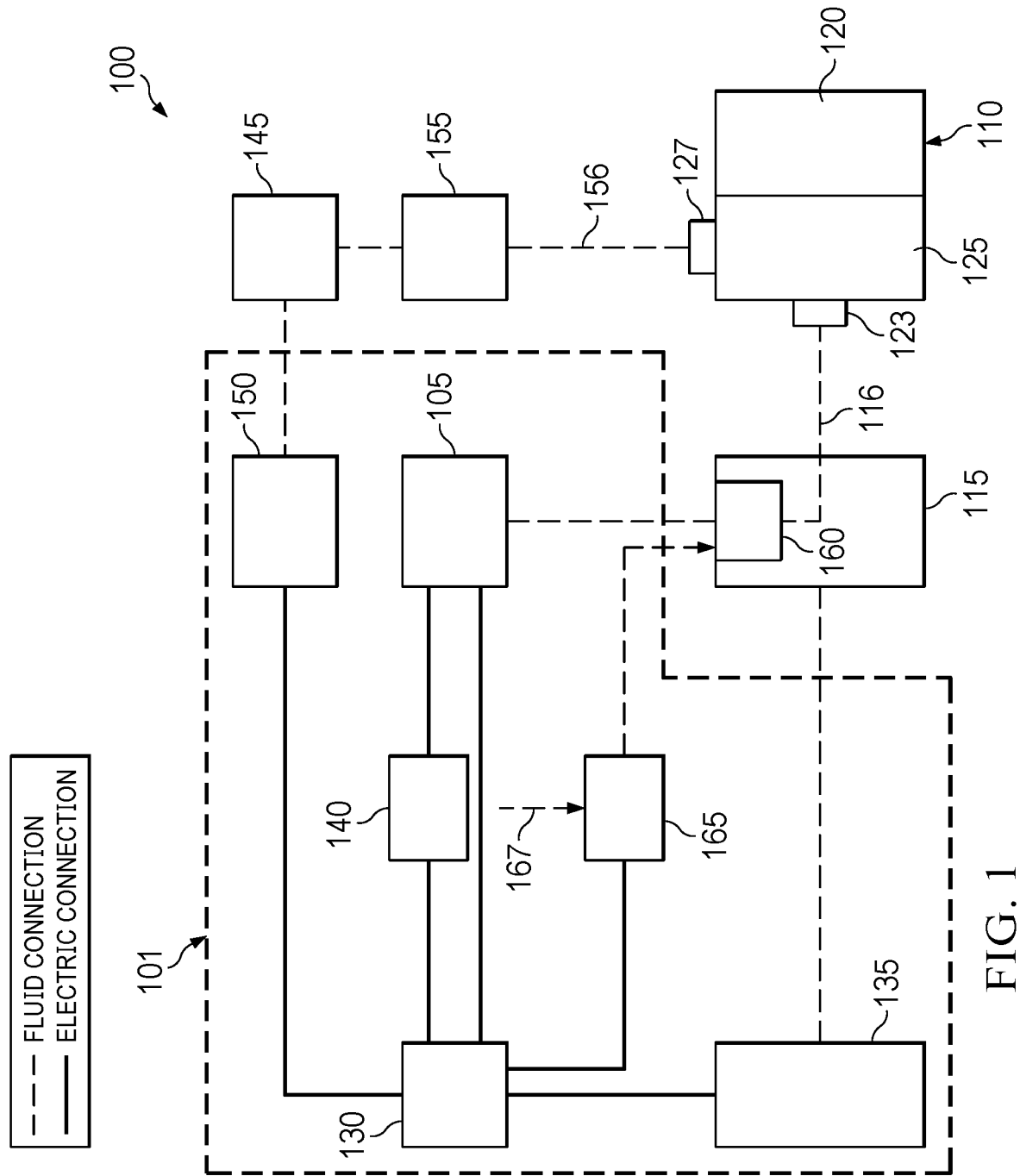
FIG. 1 is a functional block diagram of an example embodiment of a therapy system that can provide negative-pressure therapy and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface 123 may facilitate coupling a fluid conductor to the dressing 110. For example, such a dressing interface 123 may be a SENSAT.R.A.C™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source, such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110. In some embodiments, a second dressing interface 127 may facilitate coupling a fluid conductor 156 to the dressing 110 at a location removed from location of the dressing interface 123.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the first sensor 135, the second sensor 140, the regulator 165, and other components into a therapy unit 101.

In general, components of the therapy system 100 may be coupled directly or indirectly. For example, the negative-pressure source 105 may be directly coupled to the container 115 and may be indirectly coupled to the dressing 110 through the container 115 by fluid conductor 116 fluidly coupled to the dressing interface 123. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Texas Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m$^2$/24 hours and a thickness of about 30 microns.

An attachment device 142 may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

The therapy system 100 may further include one or more apparatuses containing at least one sensor for measuring one or more conditions or variables present at the tissue site and/or throughout the therapy system 100. For example, the therapy system 100 may include a diagnostic module 160, which may include one or more sensors for detecting and/or measuring one or more conditions at the tissue site. In some instances the diagnostic module may include a sensor for detecting a particular type of volatile organic compound (VOC) present at or being removed from the tissue site in wound exudates via the administration of negative-pressure therapy. For example, the levels and ratios of certain components of wound exudates may be good indicators of the stage of healing of a tissue site, and may also be useful for identifying particular issues with a wound and its associated healing progress. For example, VOC gas sensors may be useful for assessing the level of proteases in wounds to ascertain the progress of wound healing. Being able to identify high levels of proteases may often be an excellent biochemical marker for predicting poor wound healing of both acute and chronic wounds. Thus, the sensors of the diagnostic module 160 such as the VOC gas sensors provide a rapid, reliable, in situ solution for identifying the stage and/or healing of a wound at a tissue site.

In some embodiments, the sensor for detecting a particular type of VOCs present at a tissue site may be a chemical gas sensor which may detect different gases in an area, especially those gases which might be harmful to humans or animals. The chemical gas sensors may comprise many kinds of materials such as, for example, polymers, semiconductors, carbon graphites, and organic/inorganic composites which have been used as sensing materials to detect the targeted gases based on various sensing techniques and principles. Such chemical gas sensors may include, for example, acoustic wave gas sensors, resistive gas sensors, photoelectric gas sensors, and optical gas sensors.

In some embodiments, as illustrated in FIG. 1, the diagnostic module 160 may be positioned on or within the container 115 such that the fluids entering the container 115 from the tissue site may be sampled by the one or more sensors on the diagnostic module 160 in some portion of a fluid pathway or gas chamber within the container 115. The diagnostic module 160 may also be positioned at other points in the therapy system 100 such as, for example, as a component attached to the fluid conductor 116 or a component of the dressing interface 123.

In some embodiments, the diagnostic module 160 may include one or more sensors for detecting and/or measuring conditions related to proteolytic enzymes at the tissue site. Wound proteases present at the tissue site often play an important role in wound healing, and therefore, normal endogenous levels of wound proteases are important for tissue remodeling during the healing process. In normal conditions, wound proteases may break down damaged extracellular matrix (ECM) proteins and foreign material so that new tissue can form. Matrix metalloproteases (MMPs) are among the proteases typically present in wounds and can play an important role in the wound healing response.

Figure 6:
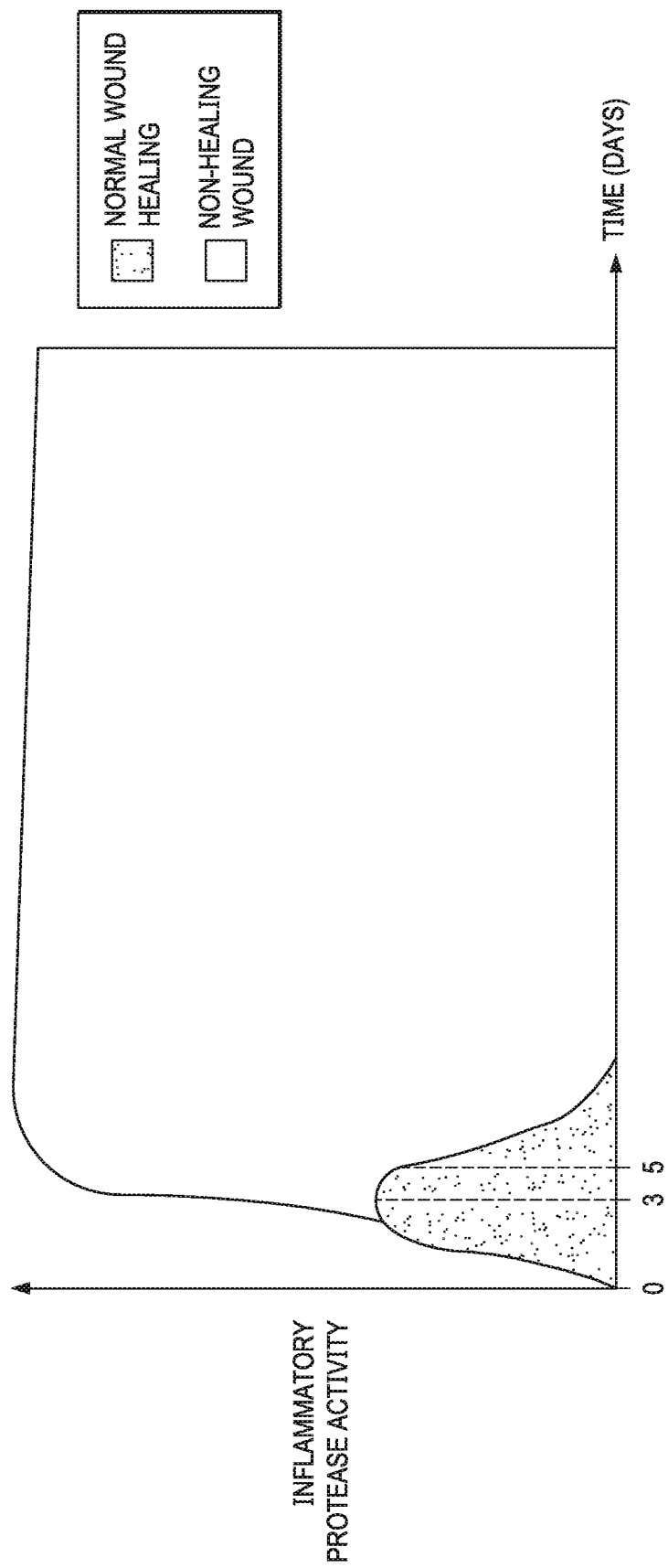
FIG. 6 is a graph of inflammatory protease activity over time for normal wound healing and non-healing wound conditions.

Wound protease activity often times is a very useful measurement of how the healing of a wound is progressing. During the initial inflammation stage of the wound healing process, there may be a higher level of protease activity. Referring to FIG. 6, protease levels initially increase rapidly in the normal course of wound healing. For example, the protease levels may peak at about the third day, but begin to reduce by about the fifth day. Thus, a directionally-changing level of protease activity may be a good indicator of normal wound healing. Thus, a directionally-changing activity from a rapidly increasing level to a decreasing level may be an indicator of normal wound healing that a device such as the diagnostic module 160 is capable of detecting by sensing one or more VOCs. However, if the level of activity increases rapidly to an abnormally high level or if the duration of the raised activity continues beyond the initial stage, it may be a good indicator that the wound is not healing as efficiently as desired. More specifically, increased levels of MMPs, often times MMP-2 and MMP-9 proteases, are commonly found in non-healing wounds. Thus, elevated protease activity may be an indicator of poor wound progress, and a device, such as the diagnostic module 160 capable of detecting the levels of the wound proteases via one or more VOCs, may be a useful tool for providing real-time feedback of wound healing to a clinician.

The therapy system 100 may also contain additional functionality for using the data related to conditions involving wound proteases in order to recommend and/or implement one or more therapeutic actions for maintaining progression of wound healing. For example, the controller 130 of the therapy system 100 may be programmed with software including algorithms for treating wounds with elevated protease activity by administering negative-pressure therapy and/or the delivery of one or more therapeutic substances to the tissue site, such as a protease-modulating compound. The controller 130 of the therapy system 100 also may be programmed software including algorithms for detecting or identifying a directionally-changing level of protease activity to indicate normal wound healing.

Additional substances and compounds may also be monitored for tracking progress of wound healing. For example, different growth factors may be associated with different stages of wound healing, such as inflammation or epithelialization. Measuring and/or monitoring the concentration ratio of such growth factors therefore may also be used as a tool to determine wound condition. Thus, in addition to elevated protease activity being a possible indicator of poor wound healing progress, raised concentration of certain growth factors may also have a detrimental effect on the healing process, such as by interfering with the ECM at the tissue site.

The therapy system 100 may further comprise a regulator 165 that may be fluidly coupled to the container 115 to provide a source of ambient air 167 from outside the container 115 to the diagnostic module 160 within the container 115. The regulator 165 may be fluidly coupled to the container 115 by a fluid conductor that forms at least a portion of a purge pathway for cleansing the sensors of the diagnostic module 160 from fluids and exudates drawn into the container 115 from the dressing 110. The regulator 165 may be any device for controlling the fluid flow of ambient air such as, for example, a passive regulator or an active regulator. In some embodiments, a passive regulator may be a device having a single opening with a known flow rate or a filter having a plurality of openings with a known flow rate, or variable regulators such as, for example, a solenoid valve or a needle valve. In some embodiments, the airflow regulator may comprise a filter that may be a hydrophillic/oeliophillic, bacterial filter having a known flow rate. Alternatively, the regulator 165 may comprise an active device such as, for example, a solenoid valve that can be controlled during intervals of negative pressure by the controller 130 that may be electrically coupled to the regulator 165 in some embodiments.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

Figure 2A:
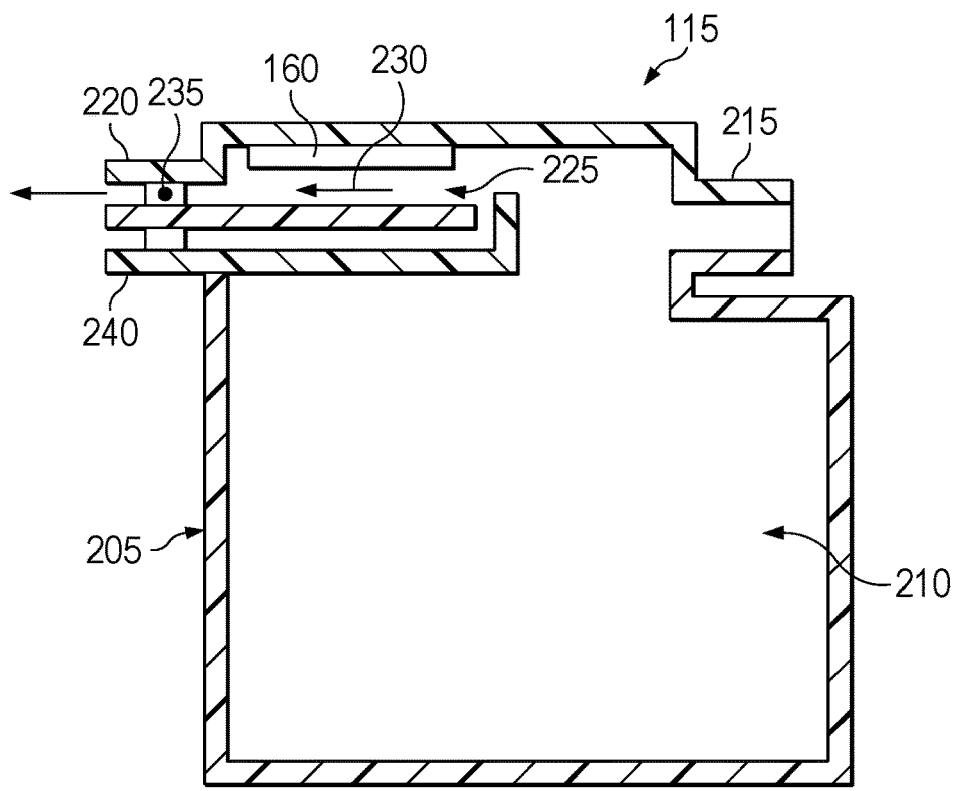
FIGS. 2A and 2B are schematic views of an example embodiment of a container for use as a component of the therapy system of FIG. 1 including a diagnostic module.
Figure 2B:
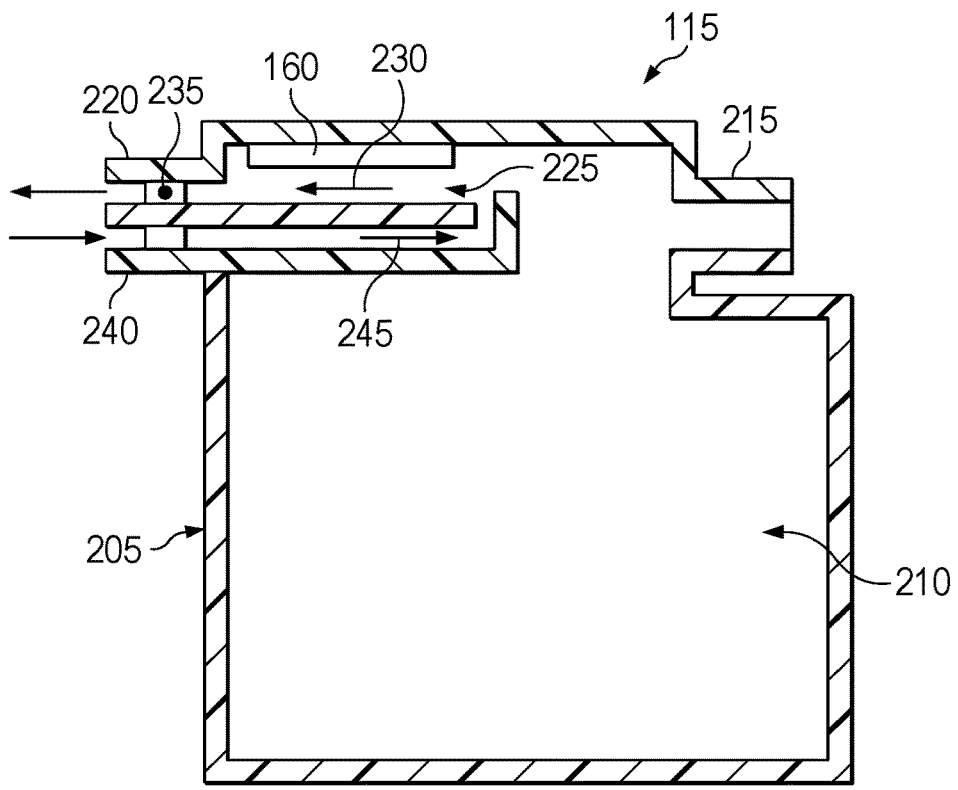

FIGS. 2A and 2B are schematic views of an example embodiment of the container 115 for use as a component of the therapy system 100 including the diagnostic module 160 showing further detail and additional features. In some embodiments, the container 115 may comprise a body 205 defining a fluid reservoir or collection chamber 210, and may be configured to be fluidly coupled between the negative-pressure source 105 and the dressing 110 to collect exudate and other fluids drawn from a tissue site into the collection chamber 210. The container 115 may also include a fluid inlet 215 and a fluid outlet 220. The fluid inlet 215 may be configured to be fluidly coupled to a conduit that is in fluid communication with the dressing 110. The fluid outlet 220 may be configured to be fluidly connected to the negative-pressure source 105. The container 115 may further comprise a gas chamber 225 fluidly coupled between the collection chamber 210 above the fluid being collected in the container 115 and the fluid outlet 220 for providing a fluid pathway 230 between the collection chamber 210 and the negative-pressure source 105 as shown more specifically in FIG. 2A. In some embodiments, the diagnostic module 160 may be disposed within the gas chamber 225 so that the sensors of the diagnostic module 160 are exposed to gases within the fluid pathway 230 that are associated with the fluids being collected in the fluid collection chamber 210 from a tissue site. In some embodiments, the diagnostic module 160 may be positioned within the fluid pathway 230 such that fluids, such as gases, may pass along, over, or under, the sensors of the diagnostic module 160 as they are drawn out of the container 115 and towards the negative-pressure source 105.

The fluid outlet 220 may include an in-line device, such as filter 235 to prevent fluid from exiting the container 115 and entering the negative-pressure source 105. For example, the filter 235 may comprise a hydrophobic filter for preventing liquid from exiting the container 115 and entering into the negative-pressure source 105. Such a hydrophobic filter may prevent liquid egress from the container 115, while allowing gases or vapor to exit. For example, a hydrophobic filter may be a hydrophobic membrane welded in an interior lumen of the fluid outlet 220. The fluid outlet 220 may allow fluid communication between the body 205 of the container 115 and the negative-pressure source 105 such that the collection chamber 210 formed by the body 205 can maintain a negative pressure. This negative pressure may be transmitted to the dressing 110 and/or tissue site through the fluid inlet 215.

The container 115 may also comprise a purge inlet 240 configured to be fluidly coupled to a conduit that is in fluid communication with the regulator 165. The purge inlet 240 may be fluidly coupled to the gas chamber 225 and/or the fluid pathway 230 to provide a purge pathway 245 as more specifically in FIG. 2B. The purge pathway 245 may provide ambient air from the source of ambient air 167 as controlled by the regulator 165 to purge or cleanse the sensors of the diagnostic module 160 within the gas chamber 225. The purge pathway 245 may be configured to provide ambient air to cleanse the sensors of the diagnostic module 160 from fluids and exudates drawn into the collection chamber 210 of the container 115 from the dressing 110 to ensure that the sensors accurately detect conditions of the tissue site for generating an output based on the detected condition.

Figure 3:
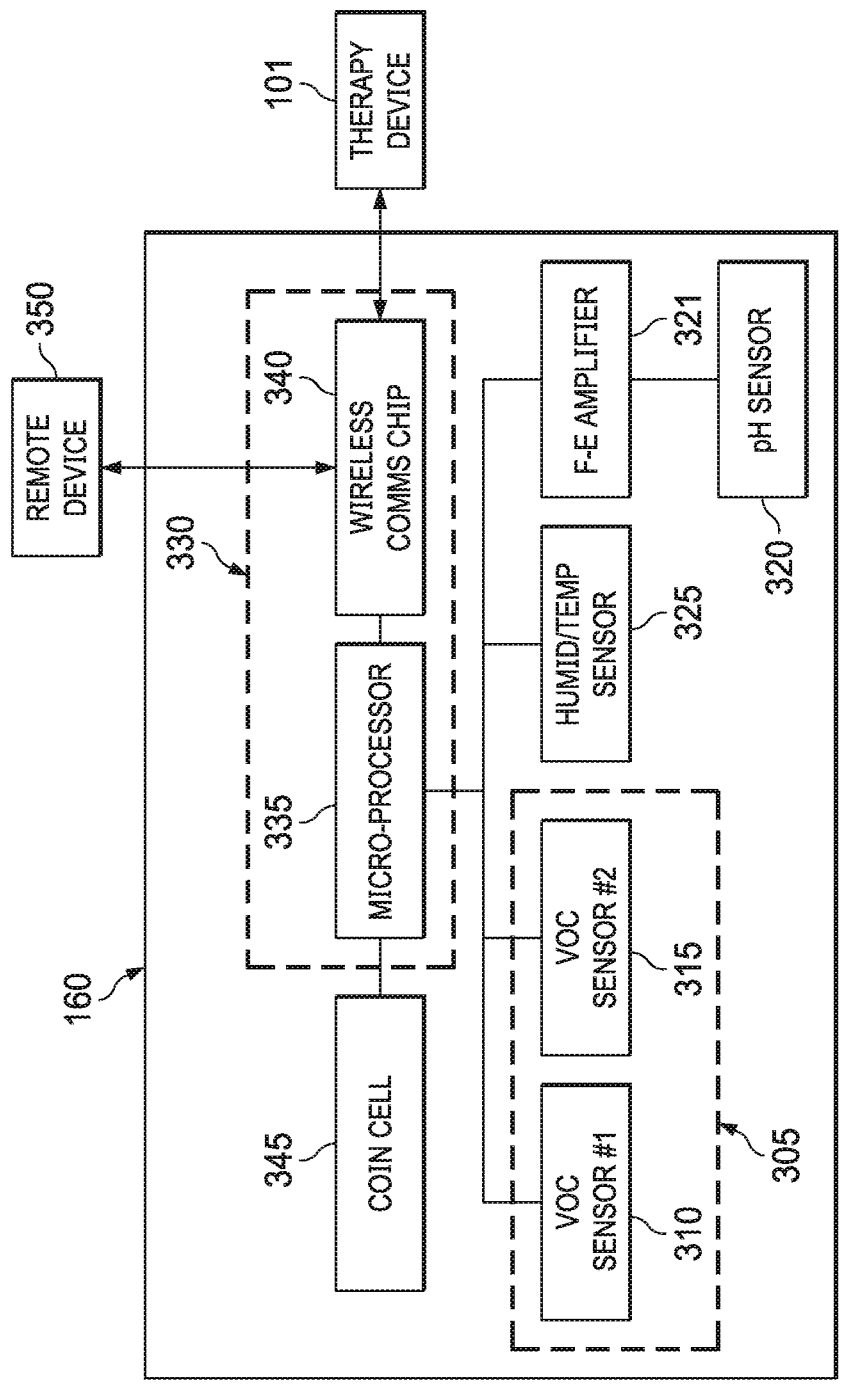
FIG. 3 is a system block diagram of the sensors and electrical devices for use as a component of the diagnostic module of FIGS. 2A and 2B.

Referring to FIG. 3, some embodiments of the diagnostic module 160 may comprise a sensor device 305 having one or more sensors configured to measure one or more parameters associated with fluids, such as gases from the environment of the tissue site. The one or more parameters measured by the sensor device 305 may be in addition to pressure measurements gathered by one or more pressure sensors, such as the first sensor 135, of the therapy system 100. For example, the sensor device 305 may comprise a first VOC sensor 310 and a second VOC sensor 315 configured to detect and/or measure one or more particular VOCs found in gases emitted from the tissue site. In one example embodiment, either one of the VOC sensors may be a FAIMS sensor available from Owlstone Medical Ltd. In another example embodiment, either one of the VOC sensors may be a sensor available from Alphasense similar to the FAIMS sensor. The FAIMS sensor in some embodiments may provide outputs or fingerprints associated with various VOCs indicative of protease levels which can be used to identify normal wound healing or non-healing wound conditions as described above. The FAIMS sensor in some other embodiments may provide other outputs or fingerprints associated with other VOCs indicative of other biomarkers which can be used to identify normal wound healing or non-healing wound conditions.

Additionally or alternatively, the sensor device 305 may be configured to detect and/or measure other parameters or variables, such as, for example, pH of wound exudates, temperature, oxygen concentration, humidity, glucose levels within wound exudates, among others. For example, the sensor device 305 may further comprise a pH sensor 320 and a humidity/temperature sensor 325. Thus, in some embodiments, the sensor device 305 may include one or more individual sensors, such as a VOC sensor, pH sensor, blood sensor, glucose sensor, growth factor sensor, or another type of sensor. Additionally, the sensor device 305 may include one or more sensors for detecting and/or measuring various electrolyte levels at a tissue site through electrical resistance sensing.

Some embodiments of the diagnostic module 160 may also comprise a communications module 330 that may include both a microprocessor 335 and a wireless communications chip 340 powered by a power source 345. The power source 345 may be, for example, a battery that may be a coin battery that provides a 3-volt source for the communications module 330 and the other electronic components associated with the sensors of the diagnostic module 160. The communications module 340 may be configured to transmit data regarding the parameters detected and/or measured by the sensors of the sensor device 305. For example, the electrical circuits and/or components associated with the sensors of the diagnostic module 160 may be electrically coupled to the controller 130 and/or other components of the therapy unit 101 by wireless means, such as an integrated device implementing Bluetooth® Low Energy wireless technology. More specifically, the communications module 330 may be a Bluetooth® Low Energy system-on-chip that includes a microprocessor such as the nRF51822 chip available from Nordic Semiconductor. The wireless communications module 330 may be implemented with other wireless technologies suitable for use in the medical environment. Alternative wireless communication protocols may also be employed, including other Bluetooth® standards, Zigbee®, ANT, Z-WAVE, or Wireless USB.

The communications module 330 of the diagnostic module 160 may be configured to transmit and receive data to/from one or more other components of the therapy unit 101, such as the controller 130, or a separate remote device 350 such as, for example, a cell phone. The controller 130 may include a communications device that is configured to communicate with the communications module 340 using the Bluetooth® 4.0 protocol. Other forms of wireless communication may also be incorporated, such as non-radio frequency technologies such as IrDA and Ultrasonic communications.

Alternatively or additionally, the sensors of the diagnostic module 160 may be electrically coupled to the controller 130 and/or other components of the therapy unit 101 via one or more wires to exchange data and control signals related to one or more parameters sensed by the sensor device 305 any other sensors of the diagnostic module 160. In such embodiments, a number of wires may be used, which may in part depend on the number of individual sensors included as part of the sensor device 305 of the diagnostic module 160. Given that multiple individual sensors may be included as part of the sensor device 305 and the diagnostic module 160, with each of the sensors potentially having different signal and communication requirements, a small interface microcontroller (not shown) may be included as part of the diagnostic module 160 to reduce the total number of wires required for communication between the sensors of the diagnostic module 160 and the controller 130. For example, a micro-controller may be capable of polling the sensors of the diagnostic module 160 and digitizing the data from the sensors so that it can be communicated to the controller 130 and/or other components of the therapy unit 101. In such embodiments, power for the diagnostic module 160 may be provided through the wired connection, while communications between the diagnostic module 160 and the controller 130 may use a Serial Peripheral Interface bus (SPI) or similar protocol to minimize the total number of wires required. Incorporating a wired solution for enabling communications between the diagnostic module 160 and the controller 130 may also increase the number and types of sensors that could be used in the diagnostic module 160 by mitigating potential power limitations of using one or more batteries for powering the sensors.

Figure 4:
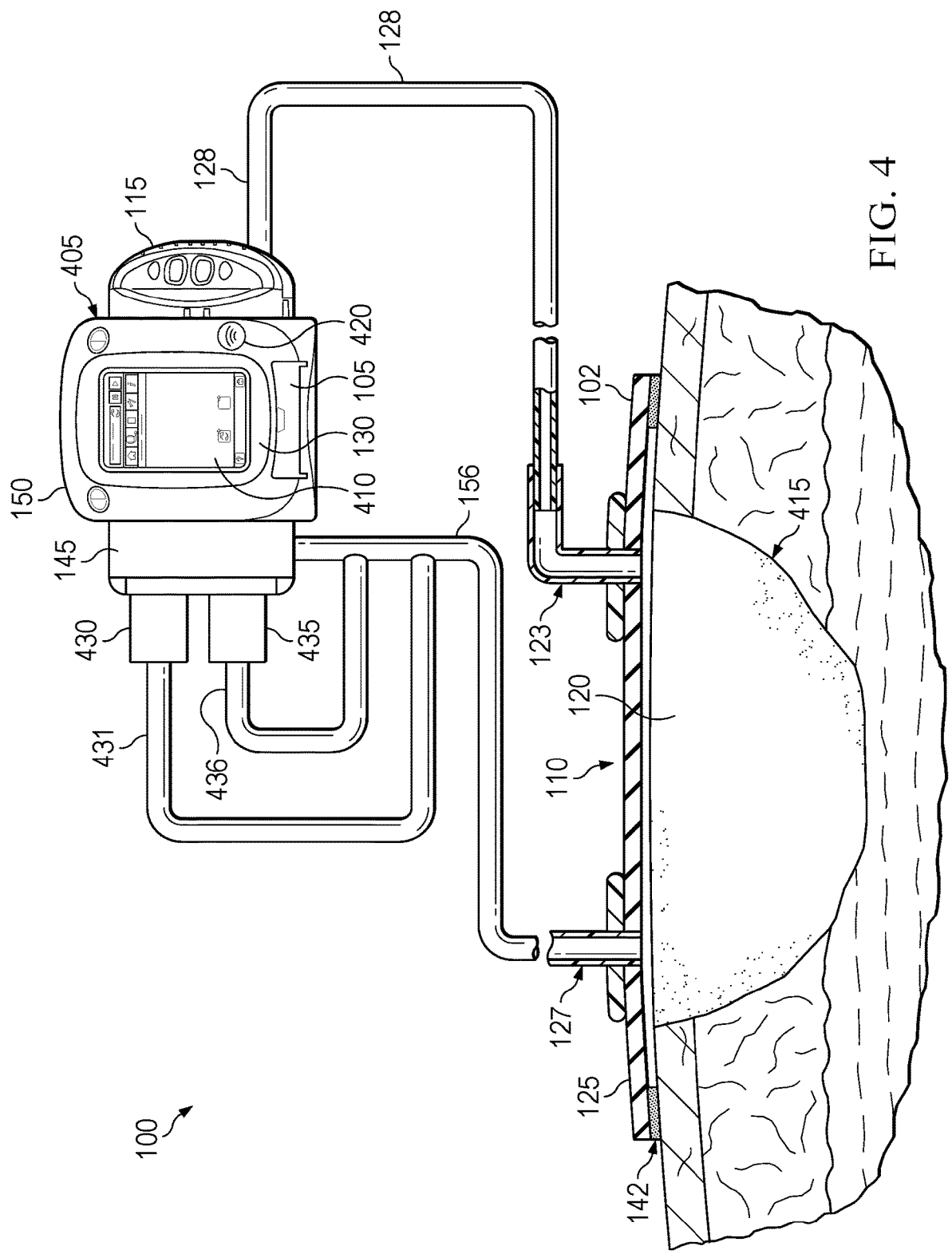
FIG. 4 is a schematic diagram illustrating additional details that may be associated with an example embodiment of the therapy system of FIG. 1.

FIG. 4 is a schematic diagram of an example embodiment of the therapy system 100, showing some further detail and additional features with respect to the therapy unit 101 that may comprise one or more components packaged as a single, integrated unit, such as therapy unit 405. For example, the therapy unit 405 may comprise the negative-pressure source 105, the controller 130, the positive-pressure source 150, and the regulator 155 (not shown in FIG. 4). The therapy unit 405 may be, for example, a V.A.C.ULTA™ Therapy Unit available from Kinetic Concepts, Inc. of San Antonio, Texas. The therapy unit 405 may also include a display unit 410, which may be a graphical user interface (GUI) configured to both display data as well as receive input from a user. The display unit 410 may be configured to display data related to the diagnostic module 160. The display unit 410 may also be configured to display information related to the delivery of negative-pressure therapy and/or fluid instillation therapy to a tissue site, such as tissue site 415. The therapy unit 405 may also include a communications device, which may be associated with the controller 130. For example, the therapy unit 405 may include communications device 420, which may be configured to exchange data with the communication module 330 associated with the diagnostic module 160. The communications device 420 may receive data from a communications module 330 of the diagnostic module 160 and communicate the data to the controller 130 of the therapy unit 405 for processing. The communications device 420 may be further configured to receive data and/or instructions from the controller 130 and transmit the data to the communications module 330 of the diagnostic module 160. The diagnostic module 160 may be positioned within or adjacent to the container 115 and, as such, may be a component of the therapy unit 405 in some embodiments. Referring more specifically to FIGS. 2A, 2B and 3, the diagnostic module 160 may be positioned within a channel or conduit fluidly coupling an interior volume of the container 115 to the negative-pressure source 105. For example, the diagnostic module 160 may be disposed in the gas chamber 225 so that the sensors are exposed to the fluid pathway 230.

Still referring primarily to FIG. 4, the therapy system 100 may further include additional sources of solution or treatment compounds or substances in addition to the solution source 145 For example, the therapy system 100 may include a first treatment source 430 and a second treatment source 435, both of which may be in fluid connection with the solution source 145 Each of the first treatment source 430 and the second treatment source 435 may include one or more compounds that may be delivered to the tissue site for therapeutic purposes. The first treatment source 430 and the second treatment source 435 may be arranged as part of the therapy system 100 so as to be able to modify a standard instillation solution provided by the solution source 145 by dosing with one or more additional compounds. The first treatment source 430 may be fluidly connected by first source conduit 431 to the fluid conduit 156 that connects the solution source 145 to the dressing 110 via the second dressing interface 127. Similarly, the second treatment source 435 may also be fluidly connected by second source conduit 436 to fluid conduit 156 Thus, in operation, as instillation fluid is being conducted from the solution source 145 to the dressing 110 through the fluid conduit 156, additional therapeutic compounds from either or both of the first treatment source 430 and the second treatment source 435 may be conducted through first source conduit 431 and second source conduit 436, respectively, and added to the instillation fluid. Additional treatment sources, such as a third treatment source and a fourth treatment source (not shown), may also be included in the therapy system 100, which may include additional treatment compounds for delivering to the tissue site.

In operation, in response to one or more parameters detected and/or sensed by the sensors of the sensor device 305, the diagnostic module 160 may transmit data from the sensor device 305 via the communications module 330 to the communications device 420 of the therapy unit 405. The controller 130 may receive data, via the communications device 420, from the diagnostic module 160 and process the data to determine one or more factors related to the tissue site 415. Based on the one or more parameters measured by the diagnostic module 160, the controller 130 may be programmed with software including algorithms capable of determining the status and healing trend of a wound at the tissue site 415. Based on an assessment of the data relating to the VOCs and/or other data provided by the particular type(s) of sensor(s) included in the sensor device 305 of the diagnostic module 160, the controller 130 may determine a progression of wound healing. For example, a change in a particular level of VOCs may signal a change in the level of MMPs at the tissue site 415, which may relate to an overall change in status of the tissue site 415. In some instances, the tissue site 415 may be considered in a healthy state if the level of MMPs present at the tissue site 415 are within a particular range. MMP levels outside of that predetermined range, such as a highly elevated amount of MMPs, may indicate that the tissue site 415 is in a chronic or inflammatory state.

In situations where the tissue site 415 may be determined to be in a chronic or inflammatory state, the controller 130 may be programmed to alert a user of the therapy system 100 as to the status of the tissue site 415 so that the user may take one or more actions to address or remedy the status of the tissue site 415. In some embodiments, the controller 130 may be programmed to generate an output or alert to a user in order to direct the user to administer one or more forms of therapy. For example, the controller 130 may indicate via the display unit 410 of the therapy unit 405 that the user should increase fluid instillation therapy as well as administer a first therapeutic compound from the first treatment source 430. Following the administration of the first therapeutic compound and fluid instillation therapy, the therapy system 100 may continue to operate and measure the effects of the administered therapy via one or more parameters measured by the diagnostic module 160. Subsequently, the controller 130 may be programmed to determine that, based on measurements taken by the diagnostic module 160, the status of the tissue site 415 has changed, and that an adjustment to one or more forms of therapy would be beneficial to the tissue site 415. For example, the controller 130 may be programmed to generate an output to the user that delivery of the first therapeutic compound from the first treatment source 430 should be suspended, while fluid instillation therapy from the solution source 145 should be increased. The controller 130 may continue to monitor the status of the tissue site 415 through parameters measured by the diagnostic module 160 and indicate proposed therapy adjustments throughout the operation of the therapy system 100.

Furthermore, in some embodiments, the controller 130 may be programmed to automatically direct that one or more types of therapy to the tissue site 415 could be initiated, adjusted, or stopped. In some embodiments, the controller 130 may automatically make changes to one or more forms of therapy, and thus the adjustments to the therapy may be triggered independently of an operator of the therapy system 100. However, the adjustments to the one or more forms of therapy may be within a set of bounds previously specified by the operator before activating the therapy system 100. In some embodiments, in response to a status of the tissue site 415 as determined by the controller 130, the controller 130 may be programmed to adjust the application of negative pressure to the tissue site 415. For example, the negative-pressure source 105 may be directed by the controller 130 to reduce or cease delivery of negative pressure to the tissue site 415 for specific time periods, such as while fluid instillation therapy is being administered to the tissue site 415. Furthermore, the controller 130 may be programmed to adjust the operation of the negative-pressure source 105 to maintain pressure levels within the dressing 110 at desired levels, based on feedback from a pressure sensor included as part of the diagnostic module 160 and/or a pressure sensor located at another portion of the therapy system 100, such as part of the first sensor 135. Additionally or alternatively, in response to the status of the tissue site 415, the controller 130 may be program to initiate the instillation of fluid, for example from solution source 145, to the tissue site 415. Further, the controller 130 may be programmed to adjust one or more properties of the fluid administered to the tissue site 415. For example, in response to a particular status of the tissue site 415 as determined by the controller 130 in response to parameters sensed by the diagnostic module 160, the controller 130 may cause a treatment compound from the first treatment source 430 to be conducted through the first source conduit 431 and added to the instillation fluid being administered to the tissue site 415. Additionally or alternatively, the controller 130 may cause a treatment compound from the second treatment source 435 to be conducted through the second source conduit 436 and added to the instillation fluid being administered to the tissue site 415.

As conditions of the tissue site 415 change over time, the controller 130 may determine a new or changed status of the tissue site 415 based on data received from the diagnostic module 160. As a result, the controller 130 may be programmed to adjust the therapy being administered to the tissue site 415. For example, in response to the changed status, the controller 130 may stop the delivery of one or both of the first treatment compound and the second treatment compound from the first treatment source 430 and the second treatment source 435, respectively. Further, the controller 130 may stop the delivery of instillation fluid from the solution source 145 altogether, and/or cause the delivery of negative pressure to the tissue site 415 to cease. Additionally, the controller 130 may provide feedback to a caregiver or the patient.

In some instances, the controller 130 may be program to determine that it would be beneficial to alternate between two forms of fluid instillation therapy. For example, the controller 130 may direct the solution source 145 to direct a first fluid, such as a saline solution, to the tissue site 415 for promotion of granulation at the tissue site 415. The controller 130 may then suspend the operation of the negative-pressure source 105 for a determined period of time to allow the saline solution to remain in contact with the tissue site 415. The controller 130 may also take into account data received from the sensors of the diagnostic module 160 when determining the length of time for allowing the saline solution to remain at the tissue site 415. Following the appropriate period of time, the controller 130 may direct the negative-pressure source 105 to resume administration of negative pressure to the tissue site 415, which may result in the removal of much of the administered saline solution. The controller 130 may be programmed to then direct that a first therapeutic compound, such as for example a collagen slurry or a collagen/ORC (oxidized regenerated cellulose) slurry, be delivered from the first treatment source 430 to the tissue site 415. A collagen/ORC slurry or solution such as, for example, a slurry or solution comprising PROMOGRAN™ material available from Kinetic Concepts, Inc. of San Antonio, Texas may be administered for controlling possible infection or levels of microbes at the tissue site 415. Other types of antimicrobial solutions or other forms of therapeutic substances may also be delivered to the tissue site 415. Once again, the negative-pressure source 105 may be powered down for an appropriate period of time, as determined by the controller 130, to allow the first therapeutic compound to take effect at the tissue site 415. Following the appropriate time period, the negative-pressure source 105 may resume operation and may deliver negative pressure to the tissue site 415, thus removing at least a portion of the first therapeutic compound from the tissue site 415. The controller 130 may also use feedback from the diagnostic module 160 to vary the level of negative pressure supplied by the negative-pressure source 105 to the tissue site 415. It should be noted that the controller 130 may automatically adjust the amount of time either form of treatment fluid remains at the tissue site 415, which may at least partially be due to feedback from the diagnostic module 160. Depending on the condition of the tissue site 415, which may in part be determined based on data received from the diagnostic module 160, the controller 130 may direct that additional cycles of alternating between two or more forms of fluid instillation therapy are warranted.

For example, one parameter measured by a sensor of the sensor device 305 of the diagnostic module 160 may be levels of one or more VOCs specific to proteases such as, for example, MMPs and serine proteases, e.g., elastase. In one example embodiment, the sensor device 305 includes the first VOC sensor 310 and the second VOC sensor 315 for sensing VOCs that may indirectly correspond to increase levels of MMPs at the tissue site 415. Raised levels of such VOCs may indirectly correspond to increased levels of MMPs at the tissue site 415 which may be an indication that the wound being monitored is healing in a normal fashion or has failed to heal as generally described above. In the normal course of wound healing, there is typically a rapid initial increase in proteases levels that peak after about three days, but start to reduce after about five days. In non-healing wounds, proteases reach higher levels than in wounds that are healing, and higher levels persist for longer period of time. The result of these higher levels is a higher destructive wound environment. Therefore, it is desirable to utilize the first VOC sensor 310 and the second VOC sensor 315 to monitor the VOCs that may be present in the gas chamber 225 and use the outputs or fingerprints from the VOCs sensors to determine the level of MMPs at the tissue site 415 in real time during therapy treatments to help guide appropriate management of the instillation and negative pressure fluids during therapy.

In some embodiments, such therapy treatments may include one or more wound healing compounds such as proteases inhibitors that may be added to the instillation fluid. More specifically, the first treatment source 430 and/or the second treatment source 435 may contain one or more wound healing compounds which may be added to the instillation fluid from the solution source 145 based on the interpretation by the controller 130 of diagnostic information from the first VOC sensor 310 and the second VOC sensor 315 of the diagnostic module 160. For example, either the first treatment source 430 or the second treatment source 435 may include, for example, a slurry or solution of PROMOGRAN™ collagen/ORC material that may be added to the instillation fluid based on a determination by the controller 130 that an infection exists at the tissue site 415. The instillation fluid containing the PROMOGRAN™ material may be effective to reduce elastase activity including both MMP-9 and human neutrophil elastase (HNE) activity to help prevent further degradation of newly formed ECMs and other proteins, e.g., growth factors and receptors.

Figure 5:
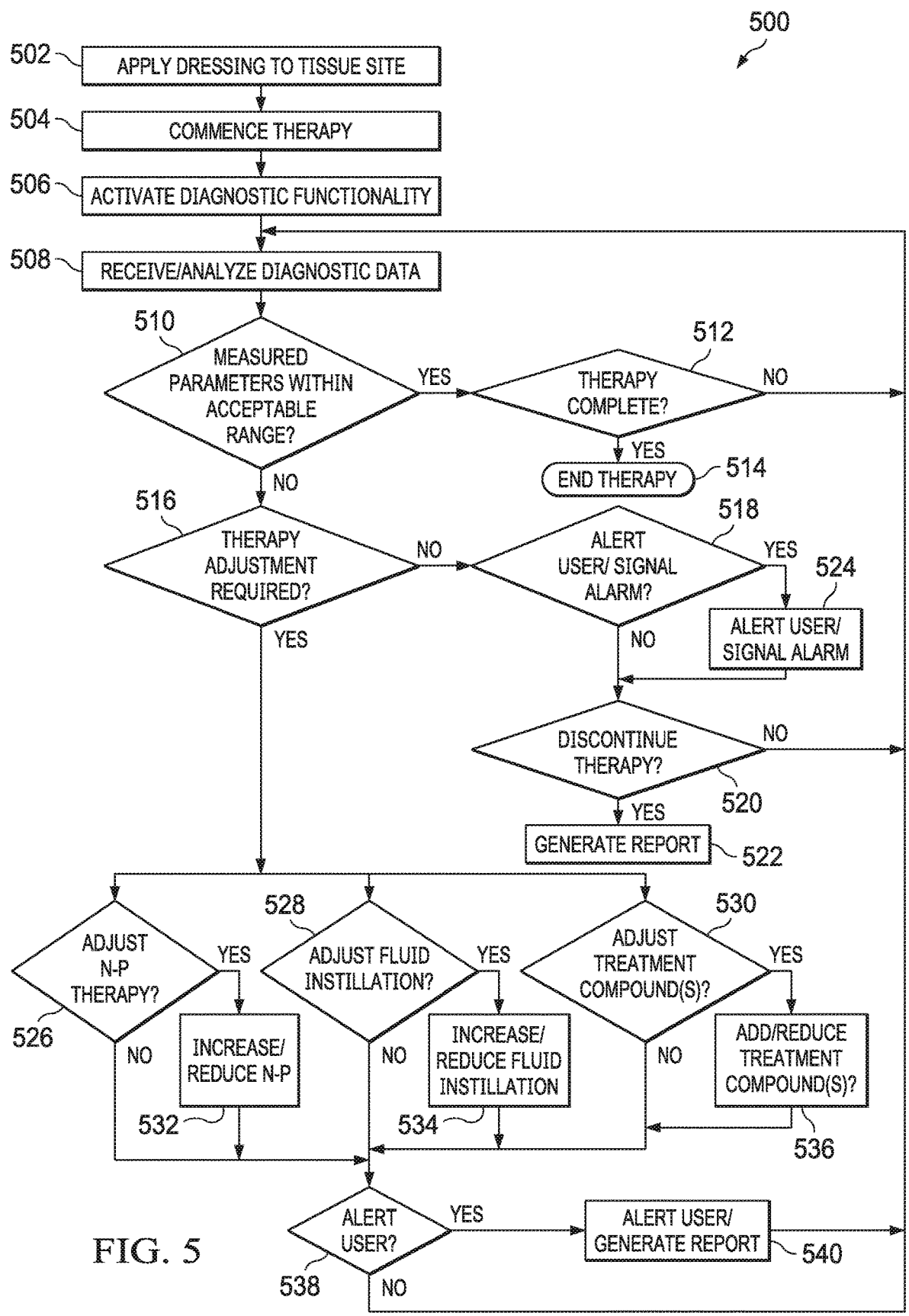
FIG. 5 is a flow chart illustrating a method of operation of the therapy system of FIG. 1, according to some example embodiments.

FIG. 5 is a schematic diagram illustrating additional details that may be associated with some example embodiments of the therapy system 100. In operation, the therapy system 100 and its various components and features may be used in accordance with the exemplary operating method 500 illustrated in FIG. 5. For example, operation of the therapy system 100 may begin with applying a dressing, such as dressing 102, to a tissue site 415, as shown in step 502. The dressing 102 may be fluidly connected to the negative-pressure source 104 by fluid conductor 128 via first dressing interface 107. The therapy system 100 may then be activated to begin delivering therapy, such as negative-pressure therapy, to the dressing 102 and tissue site 415, by fluidly connecting a negative-pressure source, such as negative-pressure source 104, to the dressing 102 and then activating the negative-pressure source 104, as shown in step 504. Step 506 shows the process of activating the diagnostic functionality of the therapy system 100, which may involve initializing a diagnostic module, such as diagnostic module 160, of the therapy system 100. Such initialization of the diagnostic module 160 may include initiating any sensors included as part of the diagnostic module 160, as well as activating a communications module, such as communications module 144, of the diagnostic module 160 to begin exchanging data with a controller, such as controller 130, of the therapy system 100. As part of such an initialization process, the controller 130 may communicate with the diagnostic module 160 to determine the types and specific versions of sensors included in the diagnostic module 160. Once the controller 130 has determined that the individual sensors of the diagnostic module 160 are compatible with the therapy system 100, the diagnostic module 160 may begin receiving signals from the sensors. As the therapy system 100 operates and delivers therapy, such as negative-pressure therapy to the tissue site 415, the one or more sensors of the diagnostic module 160 may become exposed to substances, such as wound exudates, from the tissue site environment, and the sensors may begin to collect data regarding one or more specific parameters. As previously discussed, parameters detected and/or measured by the one or more sensors may include pH of wound exudates, O2 concentration of tissue at the tissue site 415, temperature, humidity within the dressing 102, glucose level in wound exudates, as well as others.

Once the diagnostic module 160 of the therapy system 100 has begun transmitting data from the one or more sensors, the controller 130 of the therapy system 100 may receive and process the data, as depicted in step 508 of method 500. The controller 130 of the therapy system 100 may then determine whether the one or more parameters detected and/or measured by the sensor(s) of the diagnostic module 160 fall within an acceptable range, as shown in step 510. Should the controller 130 determine that the one or more measured parameters are within an acceptable range, the controller 130 may determine, as depicted in step 512, whether the desired therapy for the tissue site 415 has been completed. In some embodiments, if the controller 130 determines that therapy has been completed, the delivery of therapy, such as negative-pressure therapy, may be ceased, as depicted in step 514. However, should the controller 130 determine in step 512 that therapy has not been completed, the therapy system 100 will continue to operate to deliver therapy, and the controller 130 may continue to receive and process data from the diagnostic module 160, according to steps 508 and 510.

Returning to step 510 of method 500, should it be determined by the controller 130 that the one or more measured parameters are not within an acceptable range, the controller 130 may then determine whether an adjustment to the provided therapy or whether an additional form of therapy is necessary or would be beneficial, as shown in step 516. If it is determined that no adjustment of therapy or additional form(s) of therapy is necessary, the controller 130 may then determine whether an alert should be generated for a user of the therapy system 100. The alert may indicate that one or more parameters are outside of an acceptable range, as shown in step 518. Depending on the particular parameter that falls outside of a prescribed range, the therapy system 100 may also be configured to determine whether a visual or audible alarm should be generated. Such a user alert and/or alarm may then be generated, as illustrated in step 524. Regardless of whether an alert or alarm is generated, the controller 130 may then determine whether therapy should be discontinued given that one or more measured parameters is out of an acceptable range, as shown in step 520. If therapy is to be discontinued, the therapy system 100 may cease to provide therapy, and in some instances, a report indicating the status of the measured parameters along with other operational data may be generated, as illustrated in step 522. Otherwise, the therapy system 100 may continue to provide therapy, and the controller 130 may return to step 508 of method 500.

Referring back to step 516, should the controller 130 determine that an adjustment to therapy is warranted, the controller 130 may then proceed to a series of decision points to determine which type or types of therapy adjustments are needed. For example, as shown in step 526, the controller 130 may assess whether the amount of negative-pressure therapy should be adjusted, and if it is determined that an adjustment is needed, may make such an adjustment as shown in step 532. Additionally, the controller 130 may determine whether an adjustment to fluid instillation therapy is warranted, as depicted in step 528, which in some embodiments may result in the amount of instillation fluid, such as saline solution, to be increased, reduced, or stopped, as depicted in step 534. Further, the controller 130 may also determine whether one or more additional treatment compounds should be administered, as shown in step 530. For example, the controller 130 may determine that an antimicrobial compound should be delivered to the tissue site 415, in which case, as part of step 536, such a compound may be added to the instillation fluid being administered to the tissue site 415.

Referring again back to step 516, should the controller 130 determine that an adjustment to therapy is warranted to inhibit the level of proteases as indicated by the level of MMPs sensed by the first VOC sensor 310 and the second VOC sensor 315, the controller 130 may then proceed to a series of decision points to determine which type or types of therapy adjustments are needed. For example, such therapy treatments may include one or more wound healing compounds such as proteases inhibitors that may be added to the instillation fluid. More specifically, the controller 130 may be programmed to adjust and dispense one or more wound healing compounds at steps 530 and 536, respectively, from the first treatment source 430 and/or the second treatment source 435 that may be added to the instillation fluid from the solution source 145 based on the interpretation by the controller 130 of diagnostic information from the first VOC sensor 310 and the second VOC sensor 315 of the diagnostic module 160.

Regardless of the outcome of the decision points illustrated in steps 526, 528, and 530, the controller 130 may then determine, as depicted in step 538, whether one or more user alerts should be generated. Such an alert may then be subsequently generated and/or a report generated for a user, as shown in step 540. Regardless of such an alert, the therapy system 100 may then continue to operate according to the adjustments needed and determined by the various steps of the method 500, with the controller returning to step 508 to continue to receive and analyze diagnostic data and repeating the subsequent steps in method 500 until it is determined that therapy is completed at one of the appropriate decision points.

The systems, apparatuses, and methods described herein may provide significant advantages. For example, the ability to detect the status of a wound would be of great benefit, as healing progress may be tracked, and accordingly, treatment may be optimized to expedite closure of the tissue site. By analyzing fluid drawn off from the wound for wound factors associated with the different stages of healing, wound healing progress can be assessed. Additionally, indications of infection may be identified, thus allowing the opportunity for prompt intervention.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A system for treating a tissue site, comprising:
a dressing adapted to be placed on the tissue site;
a negative-pressure source adapted to be fluidly coupled to the dressing;
a container having a fluid inlet adapted to be fluidly coupled to the dressing, a fluid outlet adapted to be fluidly coupled to the negative-pressure source, and a collection chamber to receive fluid from the tissue site
a sensor compartment disposed within the container between the collection chamber and the fluid outlet, the sensor compartment having a fluid pathway fluidly coupled to the fluid outlet and a purge pathway configured to be fluidly coupled to an ambient environment;
a sensor module removably positioned in the fluid pathway of the sensor compartment and adapted to be exposed to gas associated with the fluid from the tissue site, wherein the sensor module comprises a first sensor configured to detect a condition of the tissue site and to generate a first output based on the detected condition;
a transceiver electrically coupled to the sensor module and configured to transmit the first output from the sensor module; and
a controller configured to:
receive the first output from the transceiver;
generate a data entry based on the detected condition; and
in response to the detected condition, adjust a provided therapy.

2. The system of claim 1, wherein the first sensor is configured to detect a first volatile organic compound.

3. The system of claim 2, wherein the first volatile organic compound comprises a bacterial component.

4. The system of claim 2, wherein the first volatile organic compound comprises a protease component.

5. The system of claim 2, wherein the first volatile organic compound comprises a matrix metalloproteinase component.

6. The system of claim 2, wherein the first sensor is any one of an acoustic wave gas sensors, a resistive gas sensor, a photoelectric gas sensor, and an optical gas sensor for detecting a volatile organic compound.

7. The system of claim 2, where the first sensor is a FAIMS sensor for detecting a volatile organic compound.

8. The system of claim 1, wherein:
the first sensor is configured to detect a first volatile organic compound; and
the sensor module further comprises a second sensor configured to detect a second volatile organic compound.

9. The system of claim 1, wherein the first sensor comprises a metal-oxide semiconductor sensor.

10. The system of claim 1, wherein the first sensor is configured to detect a first volatile organic compound indicative of the detected condition.

11. The system of claim 10, wherein the first volatile organic compound comprises a protease component.

12. The system of claim 11, wherein the detected condition is a normal wound healing condition.

13. The system of claim 12, wherein the normal wound healing condition is indicated by a predetermined low protease activity level.

14. The system of claim 12, wherein the normal wound healing condition is indicated by a protease activity level the changes from a increasing value to a decreasing value.

15. The system of claim 11, wherein the detected condition is a non-healing wound condition.

16. The system of claim 15, wherein the non-healing wound condition is indicated by a predetermined high protease activity level.

17. The system of claim 15, further comprising an instillation source adapted to be fluidly coupled to the dressing and configured to provide any instillation fluid comprising a collagen/ORC slurry when the non-healing wound condition is indicated.

* * * * *